United States Patent [19]

Lin et al.

[11] Patent Number: 4,503,208

[45] Date of Patent: Mar. 5, 1985

[54] ACRYLIC FUNCTIONAL SILICONE COPOLYMERS

[75] Inventors: Samuel Q. S. Lin, South Windsor; Steven T. Nakos, Andover, both of Conn.

[73] Assignee: Loctite Corporation, Newington, Conn.

[21] Appl. No.: 575,256

[22] Filed: Jan. 30, 1984

Related U.S. Application Data

[63] Continuation-in-part of Ser. No. 509,568, Jun. 30, 1983.

[51] Int. Cl.$^3$ .............................................. C08G 77/06
[52] U.S. Cl. .......................................... 528/15; 528/26; 528/31; 528/32; 556/437; 556/440
[58] Field of Search ................. 528/32, 31, 15, 26; 556/437, 440

[56] References Cited

U.S. PATENT DOCUMENTS

| | | | |
|---|---|---|---|
| 3,555,051 | 1/1971 | Marsden et al. | 549/215 |
| 3,746,734 | 7/1973 | Berger et al. | 526/279 |
| 3,878,263 | 4/1975 | Martin | 528/32 |
| 4,391,963 | 7/1983 | Shirahata | 528/37 |

*Primary Examiner*—Melvyn I. Marquis
*Attorney, Agent, or Firm*—Walter J. Steinkraus; Eugene F. Miller

[57] ABSTRACT

Novel copolymeric silicones including repeat units of the formula $$R_a^1 R_b^2 SiO_{(4-a-b)/2} \qquad (I)$$

and repeat units of the formula $$R_a^3 R_b^4 SiO_{(4-a-b)/2} \qquad (II)$$

where $R^1$, $R^2$ and $R^3$ are the same or different alkyl, haloalkyl, aryl, substituted aryl, alkoxy or aryloxy groups; $R^4$ is $$CH_2=\overset{R^5}{\underset{|}{C}}-\overset{O}{\underset{\|}{C}}-O-R^6-$$

where $R^5$ is H or alkyl and $R^6$ is an unsaturated divalent hydrocarbon group; a is an integer from 0–2, b is an integer from 1–3 and a+b=1, 2 or 3; and the repeat units of formula II represent no more than about 30% of the total copolymer repeat units.

The copolymers may be rapidly cured by UV light to give useful elastomers or coating films. They may also be cured with traditional peroxide methods including heat and anaerobic activated methods. They are readily prepared by hydrosilation of acrylate or 2-alkylacrylate esters of acetylenic alcohols with SiH functional silicones.

6 Claims, No Drawings

ACRYLIC FUNCTIONAL SILICONE COPOLYMERS

CROSS REFERENCE TO RELATED APPLICATION

This application is a continuation-in-part of co-pending application Ser. No. 509,568, filed June 30, 1983, the disclosure of which is incorporated herein by reference.

BACKGROUND OF THE INVENTION

This invention relates to polyorganosiloxane polymers (silicones) which have acrylic functionality thereon. As used herein, acrylic functionality refers to groups of the structure $CH_2=C(R)-C(=O)-O-$, where R is H or alkyl.

Acrylic functional silicones are desirable because they have faster and more free radical cure characteristics than do the commercially available vinyl silicones. As described in U.S. Pat. Nos. 2,956,044 and 4,035,355, methyacrylate functional silcones can be formulated with other unsaturated monomers to give monomer compositions or cured polymers with unique and desirable properties. U.S. Pat. No. 4,035,355 describes anaerobically curing compositions of methyacrylate functional siloxane polymers. U.S. Pat. No. 3,577,264 describes radiation curable film-forming paint binders utilizing acrylate or methacrylate functional siloxanes. Other patents describing methods of preparation or uses for methacrylate functional silicones include U.S. Pat. Nos. 2,793,223; 2,898,361; 2,922,806; 2,922,807, and 4,348,454 and U.K. Pat. Nos. 1,384,898 and 1,323,869.

In U.S. Pat. No. 3,878,264 there are described acrylate and methacrylate functional silicones prepared by polymerization of hydrolyzable acrylic functional silanes. Methacrylated silanes may be prepared by hydrosilation of acrylic esters of certain olefinic alcohols. Alternatively, acrylate and methacrylate functional silanes may be prepared by reacting an alkoxy or hydroxy chloroalkyl silane with a tertiary amine salt of acrylic or methacrylic acid.

An especially desirable method of preparing acrylic functional silicones is the one step hydrosilation of acrylic esters of unsaturated alcohols with SiH functional silicones. However hydrosilation of allyl methacrylate with SiH functional silicones consistently yields a product in which about 30% of the methacrylate groups grafted onto the polymer are hydrolyzable. The hydrolyzable groups result from propane elimination which produces methacrylate groups bound directly to silicone through a Si—O—C bond. The presence of these hydrolyzable methacrylate groups produces a number of problems when the polymer is exposed to moisture, including loss of methacrylate functionality and increase in viscosity of the uncured polymer due to siloxy crosslinking.

Allyl acrylate cannot be successfully hydrosilated with SiH functional silicones because addition occurs at both the allyl and the acrylate double bonds. Likewise, addition at both sites occurs in the hydrosilation of methallyl methacrylate.

In U.S. Pat. Nos. 3,555,051 and 3,746,734 there is described the preparation and hydrosilation of propargyl methacrylate with SiH functional silanes to produce alkylenyl methacrylate functional silanes, useful as adhesion promoters and sizing agents. These references also suggest that the method can be used with propargyl acrylate and further suggest preparation of homopolymers having the unit formula:

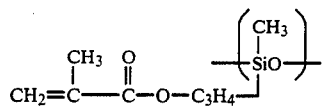

as adhesion promoters, by polymerization of the silane. Such a polymer includes acrylic functionality on each backbone silicon atom.

In copending application Ser. No. 509,568, there are described novel silicone polymers which can be obtained by the one-step hydrosilation of beta (allyloxy)ethyl methacrylate without the problem of propene elimination or addition to both unsaturated sites. Acrylic silicones produced by this method, however, are often difficult to stabilize after synthesis. Accordingly, it is desirable that alternative methods be found for the addition of acrylic functionality to SiH functional silicones.

SUMMARY OF THE INVENTION

The invention encompasses certain novel copolymeric silicones, as described below, and cured products thereof.

The present invention further encompasses a method of preparing both acrylate and 2-alkylacrylate silicones by hydrosilation of an acrylate or 2-alkylacrylate ester of an acetylenic alcohol with silicon hydride functional silicones having no more than 30% SiH containing repeat units. The SiH functional groups add quantitatively across the acetylenic bond for both acrylate and methacrylate esters and yields no observable production of hydrolyzable acrylic groups. The inventive method produces copolymeric silicones in accordance with the invention.

DETAILED DESCRIPTION OF THE INVENTION

The novel copolymeric silicones of the invention include repeat units of the formula

and repeat units of the formula

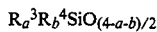

where $R^1$, and $R^2$ and $R^3$ are the same or different alkyl haloalkyl aryl, substituted aryl, alkoxy or aryloxy groups; $R^4$ is

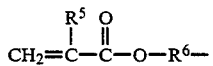

where $R^5$ is H or alkyl and $R^6$ is an unsaturated divalent hydrocarbon group; a is an integer from 0–2, b is an integer from 1–3 and a+b equals 1, 2 or 3; and the repeat units of formula II represent no more than about 30% of the total copolymer repeat units. The copolymer may be linear, cyclic or branched.

In contrast to the homopolymers suggested in the aforementioned U.S. Pat. Nos. 3,555,051 and 3,746,734, which contain acrylic functionality on each silicon atom, the present copolymers are limited to a maximum of 30% repeat units having acrylic functionality. This is necessary in order to achieve cured properties of toughness, flexibility and elasticity. Where the acrylic functionality is contained on substantially greater than about 30% of the repeat units, the subsequently cured polymer will be extremely brittle due to over-crosslinking. Even at 30% the cured products will be very hard and have limited application. More preferably, the acrylic containing repeat units will be no more than about 10% of the total polymer repeat units, still more preferably no more than about 5%. Useful curable products have been produced in which the acrylate containing repeat units were about 0.3% of the total repeat units.

The inventive copolymers are preferably prepared by hydrosilation of an acetylenic acrylic ester such as propargyl acrylate or propargyl methacrylate. A noble metal hydrosilation catalyst is used, preferably a platinum catalyst. Reaction temperatures should be kept below about 100° C. in order to prevent thermal polymerization of the acrylic groups. Examples of useful catalysts include chloroplatinic acid, platinum and hydrocarbon platinum complexes. Platinum based catalysts are preferred at levels between 10 ppm and 500 ppm platinum, preferably between 50 ppm and 300 ppm. Rhodium complexes may also be usefully employed as hydrosilation catalysts.

Acrylate versions of the inventive compounds display much faster cure speeds than corresponding 2-alkylacrylate versions. It is therefore a particular advantage of the inventive process that acrylated silicones can be prepared by a one-step hydrosilation.

Cured products of the inventive compounds also display unusual heat resistance, sometimes increasing in toughness after long-term heat aging. This effect is especially pronounced in the acrylate versions of the inventive compounds.

EXAMPLE 1

An SiH functional silicone having a MW of 9500 (as measured by GPC) and a calculated 3% of methylhydrogensiloxy repeat units was prepared by polymerization of a mixture of dimethyldichlorosilane, trimethylchlorosilane and methyldichlorosilane.

This polymer (5 grams) was then mixed with 0.23 grams propargyl acrylate in a 25 ml round-bottomed flask equipped with magnetic stirrer, thermometer and heater. The temperature was raised to about 71° C. and 0.05 grams of a 2% $H_2PtCl_6$ solution in butyl acetate was added. The reaction was continued at about 75° C. for 45 minutes, after which an IR scan showed no evidence of SiH remaining. The volatiles from the mixture were stripped.

0.5 grams of the reaction product and 1 drop diethoxyacetophenone and a thin film (0.040"–0.060" thick) was spread on a microscope slide. The slide was exposed to 70,000 microwatt/cm$^2$ UV irradiation for 45 seconds. The film cured dry to the touch and clear. The film remained clear on cooling.

The reaction product was also soluble in isobornyl acrylate. A 50% mixture of this product in isobornyl acrylate was mixed with 2% diethoxyacetophenone and cured under UV to a somewhat flexible film which remained clear on cooling.

EXAMPLE 2

50 grams of a 12,400 MW SiH terminated dimethylsilicone was mixed with 1.02 grams propargyl acrylate, 0.31 grams of a 2% acid solution, 0.01 grams butylated hydroxy toluene and 50 ml benzene. The mixture was heated to 70° for three hours. The mixture was stripped as before, giving 50.4 grams of a light yellow product.

A thin film of the product mixed with 2% diethoxyacetophenone cured flexible after 30 seconds UV irradiation per side.

EXAMPLE 3

A 1000 MW SiH terminated dimethyl silicone was used to prepare a polyphotoinitiator from alpha-allylbenzoin ethyl ether in the manner of U.S. Pat. No. 4,391,963 and copending application Ser. No. 505,588, filed June 20, 1983, the disclosures of which are incorporated herein by reference.

10 grams of the same SiH terminated silicone were then mixed with 2.18 grams propargyl acrylate and 0.1 grams of a 2% chloroplatinic acid solution. The mixture was heated to about 70° C., producing a reaction exotherm to 140° C. The product was stripped after the exotherm had subsided. Equal amounts of the propargyl acrylate product and the polyphotoinitiator product were mixed, spread as a thin film and irradiated as in Example 1 for 10 seconds. The cured film remained clear on cooling.

EXAMPLE 4

This example demonstrates the unexpected heat aging properties of the cured properties of the acrylate functional silicones of the invention compared to cured properties of similar known methacrylate functional silicones.

Acryloxpropenyldimethylchlorosilane was prepared by a modification of Example 2 of U.S. Pat. No. 3,746,734, using propargyl acrylate and dimethylchlorosilane as starting materials. Two silicone resins in accordance with the invention were then prepared by reaction of acryloxypropenyldimethylchlorosilane with diethylamine, followed by condensation with dimethylsilicones terminated on both ends with silanol groups. One of the silanol silicones had an average molecular weight of 12,000 and its condensation product is designated Acr-12K. The second silanol silicone was a 28,000 MW resin and its reaction product is designated Acr-28K.

For comparison, 2-methacryloxypropyl terminated silicones were prepared from methacryloxypropyldimethylchlorosilane and the same silanol terminated silicones, by the same method. These products are designated Macr-12K and Macr-28K, respectively. Such silicones are known in the prior art.

A composition was then formulated from 20% by weight of a high surface area dimethyldichlorosilane treated silica sold by DeGussa under the name Aerosil R974 and 40% each of the Acr-12K and Acr-28K silicones. A second composition was prepared with 20% Aerosil R974 and 40% each of the Macr-12K and Macr-28K silicones. To each formulation (98 parts) was then added 2 parts by weight diethoxyacetophenone. The resulting compositions, designated PA and Control, respectively, were then cast as 80 mil films and exposed to 70,000 milliwatt/cm$^2$ UV irradiation until cured. The PA composition was completely cured after one minute per side exposure. The control required two minutes per side to assure complete cure.

Tensile strength at break, tear resistance and percent elongation at break of the cured products were measured on unaged samples and on samples aged for one, two and four weeks at 350° F. per ASTM D-412, D-412 and D-624, respectively. The results (averages of four samples) are listed in Table I and demonstrate the superior heat aging properties of the cured silicones of the invention.

TABLE I
Heat Aging of Cured Silicone Rubbers

| | | Control | PA |
|---|---|---|---|
| Tensile | unaged | 233 | 398 |
| (psi) | 1 wk. | 218 | 552 |
| | 2 wks. | 238 | 566 |
| | 4 wks. | 252 | 536 |
| Tear | unaged | 64 | 54 |
| Resistance | 1 wk. | 55 | 57 |
| (lb./in.) | 2 wks. | 53 | 51 |
| | 4 wks. | 50 | 48 |
| Elongation | unaged | 194 | 144 |
| (%) | 1 wk. | 107 | 246 |
| | 2 wks. | 100 | 208 |
| | 4 wks. | 93.5 | 196 |

We claim:

1. A method of preparing an acrylic functional copolymer comprising reacting by hydrosilation reaction a silicon hydride functional silicone copolymer comprising repeat units of the formula $$R_a^1 R_b^2 SiO_{(4-a-b)/2} \quad (I)$$

and repeat units of the formula $$R_a^3 R_b^{4'} SiO_{(4-a-b)/2} \quad (II)$$

where $R^1$, $R^2$ and $R^3$ are the same or different alkyl, haloalkyl, aryl, substituted aryl, alkoxy or aryloxy groups; $R^{4'}$ is H; a is an integer from 0–2, b is an integer from 1–3 and a+b=1, 2 or 3; and the repeat units of formula II represent no more than 30% of the total copolymer repeat units, with an acrylic ester of an acetylenic alcohol having the formula $$\underset{CH_2=C-C-O-R^{6'}}{\overset{R^5 \quad O}{\underset{|\quad\;\;\|}{}}}$$

where $R^5$ is H or alkyl and $R^{6'}$ is an acetylenic hydrocarbyl group.

2. A method as in claim 1 wherein the hydrosilation reaction is conducted at a temperature below about 100° C.

3. A method as in claim 1 wherein the hydrosilation reaction is conducted in the presence of a platinum or rhodium catalyst.

4. A method as in claim 1 wherein said acrylic ester is propargyl acrylate.

5. A method as in claim 1 wherein the said silicon hydride functional silicone contains no more than 10% silicon hydride containing repeat units.

6. A method as in claim 1 wherein between about 0.3% and 5% of the repeat units in said silicon hydride functional silicone are silicone hydride functional repeat units.

* * * * *